(12) United States Patent
Wosnitza et al.

(10) Patent No.: US 6,860,848 B2
(45) Date of Patent: Mar. 1, 2005

(54) UROLOGICAL RESECTOSCOPE FOR CHILDREN

(75) Inventors: Thomas Wosnitza, Lüneberg (DE); Jorg Dickopp, Reinbeck (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 25 days.

(21) Appl. No.: 10/343,340

(22) PCT Filed: Feb. 6, 2002

(86) PCT No.: PCT/EP02/01198

§ 371 (c)(1),
(2), (4) Date: Jan. 29, 2003

(87) PCT Pub. No.: WO02/096305

PCT Pub. Date: Dec. 5, 2002

(65) Prior Publication Data

US 2003/0144662 A1 Jul. 31, 2003

(30) Foreign Application Priority Data

May 30, 2001 (DE) ........................ 101 26 541

(51) Int. Cl.[7] ............................... A61B 1/00
(52) U.S. Cl. ...................... 600/105; 606/46
(58) Field of Search ............... 606/41, 45, 46, 606/49, 170, 180; 604/22; 600/101, 107, 108–109, 100, 119, 104–105

(56) References Cited

U.S. PATENT DOCUMENTS

| 4,648,399 A | 3/1987 | Nakada |
| 5,088,998 A | 2/1992 | Sakashita et al. |
| 5,287,845 A | 2/1994 | Faul et al. |

Primary Examiner—John P. Leubecker
Assistant Examiner—Pete Vrettakos
(74) Attorney, Agent, or Firm—Rankin, Hill, Porter & Clark, LLP

(57) ABSTRACT

A urological resectoscope includes a main casing and an optic guide plate mounted proximally to and a fixed distance from the main casing. A slider is displaceably guided between the main casing and the optic guide plate. A drive rod is detachably affixed to the slider at a first distance from an optic tube longitudinally passing through the resectoscope and in a first angular position to the grip, said rod running from the slider, parallel to the optic tube, through the main casing and then in a second angular position relative to the optic tube and at a second, minute distance from it, and the optic tube together with matched, tightly enclosing stem tube of matched cross-section running as far as said stem tube's distal end zone, the drive rod supporting a surgical implement, characterized in that a free space corresponding at least to the excursion of the drive rod is provided in the main casing and is fitted in the region of the free space with a deviation site where it is pivoted out of the first angular position and first distance from said optic tube into the second angular position and the second distance.

6 Claims, 2 Drawing Sheets

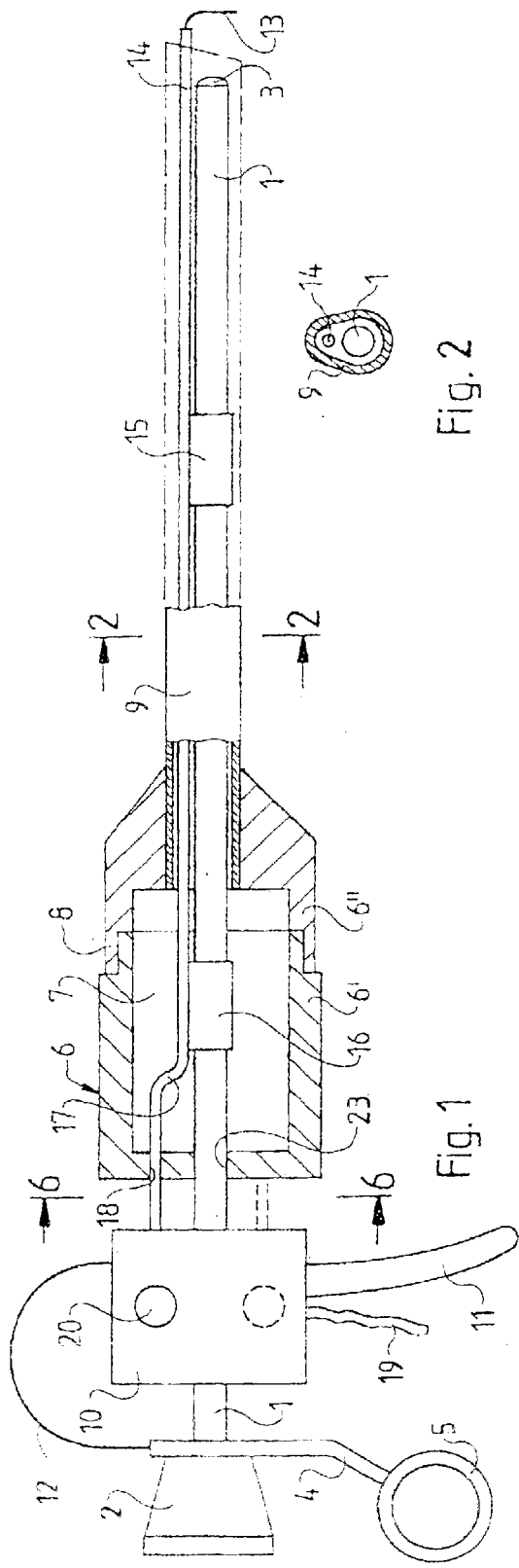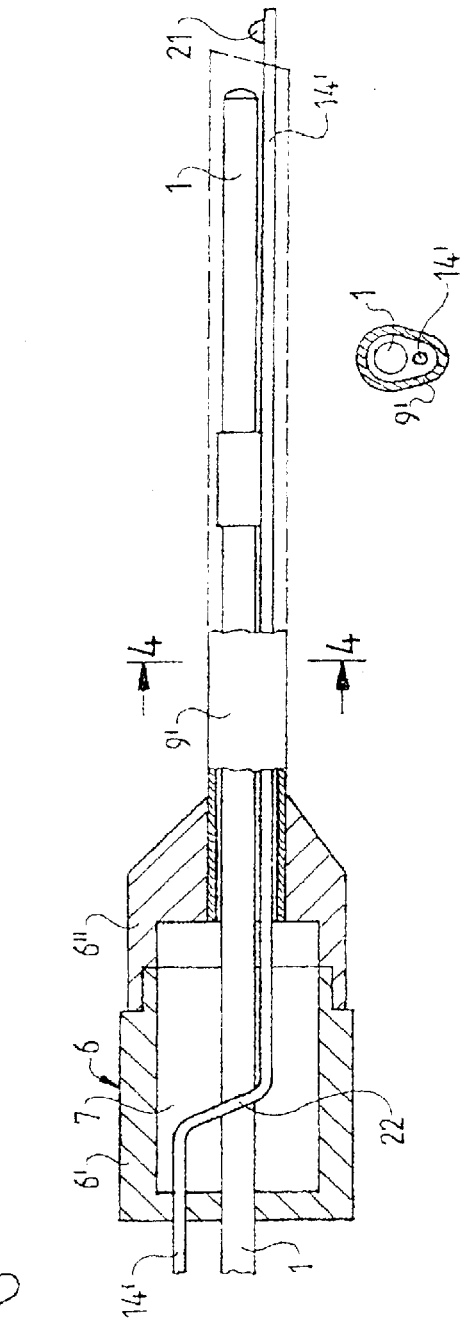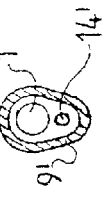
Fig. 1
Fig. 2
Fig. 3
Fig. 4

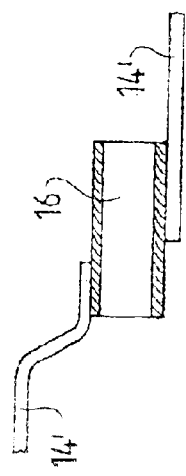
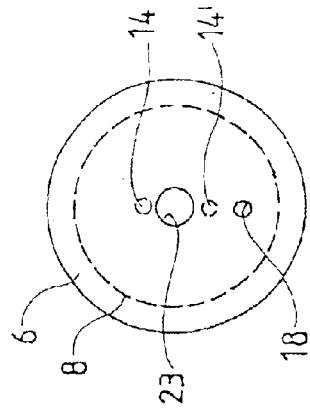
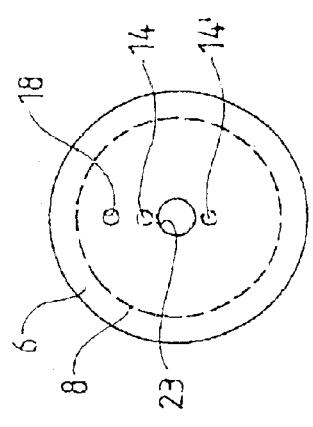
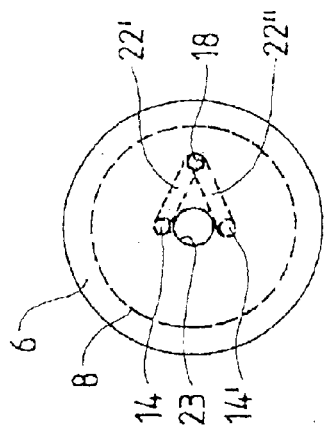

UROLOGICAL RESECTOSCOPE FOR CHILDREN

BACKGROUND OF THE INVENTION

1. Field of the Invention

The present invention relates to a urological resectoscope and, more specifically, toward urological resectoscopes for children.

2. Description of Related Art

Such resectoscopes require being fitted with an especially narrow stem tube so they may be used in the still very narrow juvenile urethra. Accordingly, the stem tube encloses, by its almost pear-like, shape-matched cross-section, the cross-sections of the drive rod and of the optic tube. To minimize the cross-sections, the otherwise conventional double-tube design used in resectoscopes to create a second rinsing duct is eliminated.

A children's resectoscope of this kind is known from the applicant's catalog TRANSURETHRALE RESEKTION, pp 30–32, 1997. Catalog # A3753 on page 32 relates to and shows a surgical insert of which the surgical implement is a cutting loop. With respect to the grip situated below the operational direction, the cutting loop must be affixed above and, accordingly, the drive rod constituting the electrode support must run above the optic tube. In the known design, the cutting loop runs above the optic tube through the main casing as far as the slide element in which it is detachably affixed and with which it makes electrical contact. The resectoscope is shown without the associated stem tube A3750 and is denoted by the catalog #A3752.

Surgery involving children's urological resectoscopes in addition to an hf-loaded cutting loop also always require a cold knife with a cutting blade projecting from the drive rod. However, surgical conditions also require, in this respect, that the cutting blade project from bottom to top. As a result, the drive rod of such designs, which is shown on the cited catalog page by #A3748, must be mounted underneath the optical tube. The state of the art requires a second resectoscope, which is shown under catalog #A3745 without the associated stem tube A3744, where the drive rod runs underneath the optic tube as far as the slide element to which it is affixed.

Because the full resectoscope must be manufactured in two designs, the substantial added costs entail a drawback.

SUMMARY OF THE INVENTION

An objective of the present invention is to create a resectoscope of the above species for which the costs of employing the two surgical procedures shall be reduced.

According to the invention, the drive rod shall be deviated, within a free space of the main casing, from its angular position at the slider into the angular position in the stem zone. Only at this location, that is in the main casing, does the design of the resectoscope offer the opportunity for such deviation, because otherwise a proximal displacement from the main casing would shorten the slider's excursion range and no space would be available for such a displacement in the narrow stem tube. The invention therefore creates a resectoscope requiring only changing the stem tube or mounting it in another angular position. When the first angular position—namely the affixation of the drive rod on the slider—illustratively is above the optic tube, then the cold-knife drive rod may be designed having a deviation site while the drive rod actuating the hf cutting loop is conventional and straight. The main part of the expensive resectoscope can, thus, be used for both surgical methods. Only the drive rod with the surgical implement (hf cutting loop or cold knife) needs changing, which is required anyway. Again the stem must be changed or rotated.

In further accordance with the present invention, the guide tube assures secure guidance of the drive rod to the optic tube within the free space in the main casing and as a result lateral, undesired motions are precluded. Illustratively, this guide tube may be in addition to another one, which, in apparatus of the state of the art, does guide the drive rod in the stem zone on the optic tube.

In further accordance with the present invention, design of the deviation site is especially compact because—besides the very thin-walled guide tube at the deviation site—elements of the drive rod are present only in the two angular positions. Any additional intermediate zone of the drive rod, which would be pivoted about the optic tube and which would entail additional bulk, is thereby eliminated.

BRIEF DESCRIPTION OF THE DRAWINGS

These and further features of the invention will be apparent with reference to the following description and drawings, wherein:

FIG. 1 is a partly sectional sideview of a resectoscope of the invention fitted with an hf cutting loop;

FIG. 2 is a section as seen along line 2—2 in FIG. 1;

FIG. 3 partly represents FIG. 1 in the cold-knife embodiment;

FIG. 4 is a section as seen along line 4—4 of FIG. 3;

FIG. 5 shows the deviation site of the drive rod of FIG. 3 in another embodiment;

FIG. 6 is a section as seen along line 6—6 of FIG. 1; and,

FIGS. 7 and 8 are schematics similar to FIG. 6 of other resectoscope embodiments.

DETAILED DESCRIPTION OF THE PREFERRED EMBODIMENTS

FIG. 1 is a partly sectional view of a resectoscope of the invention. An optic tube 1 receives in removable manner,(for instance for cleaning purposes), an optics with a proximal ocular 2 and a distal objective 3. An optics guiding plate 4 fitted at its bottom with a thumb ring 5 is affixed at the proximal end of the optics tube 1.

A main casing 6 is affixed on the optics tube a distance from the optics guiding plate 4 and subtends a free space 7 around this optics tube 1. In the embodiment shown, the main casing 6 is a hollow housing.

A stem tube 9 shown mostly in dashed lines is detachably affixed on a flange 8 at the distal end of the main casing 6.

In the embodiment shown in FIGS. 1 and 3, the casing 6 consists of two parts 6', 6" that may be joined to each other at the flange 8. The proximal part 6' of the main casing is affixed to the optics tube 1. The detachable, distal part 6" is affixed to the stem tube 9 and constitutes the stem tube's coupling for connection to the main casing 6.

A slider 10 is fitted at its underside with a grip 11 for the surgeon's index finger and is displaceably supported on the optics tube 1 between the optics guiding plate 4 and the main casing 6. A leaf spring 12 connects the optics guiding plate 4 and the slider 10.

The surgeon's hand on the grip underneath the resectoscope defines the direction of "bottom". When the thumb ring 5 and the grip 11 are seized by the thumb and index finger, the slider 10 may be moved against the opposing force of the leaf spring 12.

The resectoscope of FIG. 1 is designed for high-frequency cutting by means of a cutting loop 13 seated on a drive rod 14 constituting the electrode support. For effective cutting, the cutting loop 13 must project from above in front of the field of view of the objective 3. In the zone of the stem tube 9, the drive rod 14 must run, therefore, above the optics tube 1. The drive rod 14 is guided in longitudinally displaceable manner by a guiding tube 15.

As shown cross-sectionally in FIG. 2, the stem tube 9 encloses, in a narrow, pear-shaped cross-section, the tightly adjacent cross-sections of the drive rod 14 and of the optics tube 1. In this manner, the least periphery is assured for the stem tube 9.

As shown by FIG. 1, the drive rod 14 runs in the proximal direction parallel to and tightly against the optics tube 1 through the region of the stem tube 9 as far as into the free space 7 of the main casing 6. There, it is guided by a further guide tube 16 in an additionally securing manner on the optics tube 1 and, there, it increases by means of a pivoting element 17 its distance from the optics tube 1 in order that next it shall run parallel to the optics tube 1 through a borehole 18 in the proximal end wall of the main casing 6 as far as the slider 10. There, the proximal end piece of the drive rod 14 is inserted into a receiving borehole and makes electrical contact in a manner not shown with an electrical cable 19 and is, illustratively, clamped by the shown clamping screw 20.

FIG. 3 is a distal partial elevation of the resectoscope of FIG. 1 that, therefore, is identical inclusive the main casing 6 and its elements proximal from the casing with the embodiment of FIG. 1.

In the embodiment of FIG. 3, the resectoscope is designed for cold cutting using a cutting blade 21 which, due to surgical requirements, must project from below the optical tube 1 upward as shown in FIG. 3. As a result, the drive rod 14' must run through the stem tube 9' underneath the optic tube 1, with the cross-section of the tube 9' also being very narrow.

Because the proximal end zone of the resectoscope is the same as that of FIG. 1 and, hence, the drive rod 14' is affixed also above the optic tube, this drive rod 14' is laterally deviated at the slider 10 in the free space 7 of the main casing 6 at a deviation site 22 about the optic tube 1 from the distance to this optic tube that it assumes in the stem tube 9' and from the angular position in this zone (bottom) into the required distance and the angular position (at a larger distance and at the top). The deviation site 22 requires space around the optic tube 1 and is situated in the free space 7 of which the length is such as to allow shifting the deviation site 22 as the slider 10 is displaced.

As shown in the Figures, the main casing 7 consists of its two parts 6', 6". In another embodiment, the main casing may consist of only one of the two parts, for instance the part 6" supporting the stem tube 9.

As shown by comparison with FIGS. 2 and 4, the embodiment of FIG. 3 entails changing the optic tube 9' relative to the optic tube 9 of the embodiment of FIG. 1. However, the same tube also might be used in an angular position rotated by 180°.

FIG. 5 shows the deviation site 22 of another embodiment. In this case the guiding tube 16, already shown in FIG. 1, is being used, and to which is affixed the drive rod 14' of FIG. 2 in a split embodiment. As shown by FIG. 5, a proximal part of the drive rod 14' is affixed, for instance by soldering/welding, from above on the guiding tube 16, and a distal segment from below. As a result, and as shown in FIG. 3, the lateral enclosure of the optic tube 1 at the deviation site 22 and, hence, the entailed lateral space requirement, shall then be economized.

FIG. 6 is a cross-section along line 6—6 of FIG. 1 of the proximal end face of the main casing 6 exhibiting a central borehole 23 through which passes the optic tube that is also affixed to it. FIG. 6 also shows the borehole 18 passing the drive rod 14 or 14' proximally to the slider 10. The distal flange 8 of the main casing 6 is also shown in dashed lines. Moreover, the positions of the drive rod 14 of FIG. 1 and of drive rod 14' of FIG. 3 also are shown in dashed lines.

FIG. 7 elucidates a resectoscope embodiment variation in which, contrary to the case of the above embodiment, the drive rod is affixed to the slider 10 below the optic tube 1, as indicated by dashed lines for the drive rod and the clamping screw 20 in FIG. 1. As shown by FIG. 7, the borehole 18 in this embodiment is configured underneath the borehole 22. If, in this case, the drive rod 14 with distal cutting loop were employed—which proximally of the main casing 6 must assume the position shown in FIG. 7—then it would have to be provided with the deviation 22, for instance as shown in FIG. 3, inside the main casing 6 in order to be able to run from there deviated downward through the borehole 18 to be affixed below at the slider 10. If the drive rod 14' with knife blade 21 is used, then it might run inside the main casing 6 while being pivoted by the simple pivoting element 17 through the borehole 18.

In the manner of FIGS. 6 and 7, FIG. 8 shows a further embodiment of the resectoscope of the invention. In this embodiment, the drive rod is affixed to the omitted slider 10 laterally of the optic tube 1 that is, for instance, according to FIG. 1, being shifted to the observer relative to the plane of the drawing. Accordingly, the borehole 18 running to the slider 10 is configured laterally, namely next to the borehole 23 receiving the slider 10. As regards the stem region, the rods 14 or 14' which again are, respectively, situated top and bottom are required in this design too, depending on the hf cutting method of FIG. 1 or the cold cutting method of FIG. 3 being used. Deviation sites 22' and 22" must be provided in the main casing 6—that is in its free space 7—for the drive rods 14 and 14', resp., the sites implementing the distance adjustment relative to the optic tube 1 and the angular displacement of 90° to either side.

The shown design represents a resectoscope with a so-called active transport, whereby the cutting loop 13 is manually retracted against the opposing force of the leaf spring 12 and wherein the loop is forced forward solely by the force of the leaf spring 12. However, so-called passive transports are often used. The resectoscope of the invention also may be designed in this manner. In that case the thumb ring 5 must be affixed to the slider 10 and the grip 11 to the main casing 6. Also the leaf spring 12 must be configured between the slider 10 and the main casing 6. In that case, the cutting loop 13 is advanced against the spring force and the loop shall be automatically forced back by it (passive cutting).

In both the shown embodiment and in its variant just discussed above, the leaf spring 12 assumes the form of a spring forcing apart the two parts it connects. However, it also may be designed as a contracting spring. In that case and with respect to FIG. 1, the thumb ring 5 and the grip 11 shall be unchanged and the spring shall be configured between the slider 10 and the main casing 6. Such an embodiment also may be applied to the above-cited passive transport.

What is claimed is:

1. A urological resectoscope for children, comprising:

a main casing (6);

a distally extending stem tube (9, 9') that is adapted to be coupled to said main casing (6);

an optic guide plate (4), said optic guide plate being mounted at a fixed distance from said main casing;

a slider (10), said slider being displaceably guided between said main casing and said optic guide plate;

an optic tube (1), said optic tube extending longitudinally through said resectoscope;

a drive rod (14, 14'), said drive rod being releasably secured to said slider at a first radial distance and a first angular position from said optic tube, extending from the slider parallel to the optic tube into the main casing, and then extending at a second radial distance and a second angular position and parallel to the optic tube through the stem tube, said first radial distance being greater than said second radial distance, wherein said stem tube tightly encloses the drive rod and the optic tube, and wherein a distal end of said drive rod projects from a distal end of said stem tube and supports a surgical implement;

wherein a free space (7) is provided in the main casing (6), said free space having a length corresponding at least to a desired range of motion of the drive rod (14, 14'), the drive rod comprising a deviation site (22, 16, 22', 22") disposed within the free space wherein said rod is angled relative to the optic tube (1) so as to change from the first radial spacing at the first angular position to the second radial spacing at the second angular position.

2. The resectoscope as claimed in claim 1, further comprising a guide tube (16), said guide tube being disposed in the free space, surrounds the optic tube (1), and is affixed to the drive rod (14, 14').

3. The resectoscope as claimed in claim 2, wherein the drive rod (14') is formed in a first part and a second part, said first part comprising a proximal portion of said drive rod and is affixed at its distal end to the guide tube, said second part comprising a distal portion of said drive rod and is affixed at its proximal end to said guide tube.

4. The urological resectoscope according to claim 1, wherein said first angular position is offset 180° from the second angular position.

5. The urological resectoscope according to claim 1, wherein said first angular position is offset 90° from the second angular position.

6. The urological resectoscope according to claim 1, wherein said first angular position is offset from the second angular position an amount that is greater than 0° and less than or equal to 180°.

* * * * *